Figure 1:
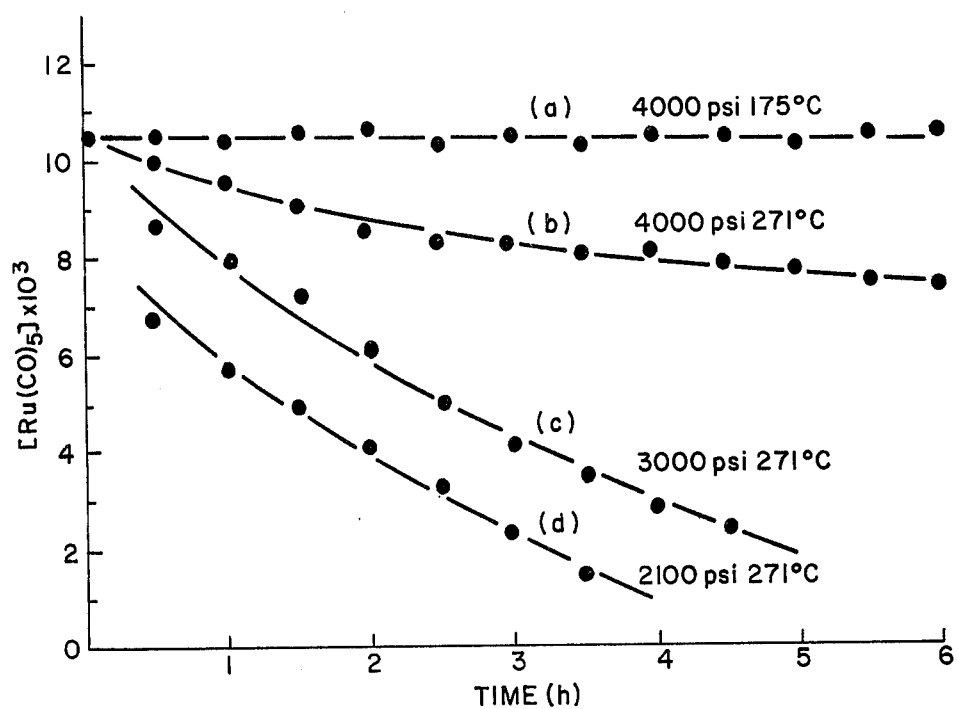

United States Patent [19]

Bradley

[11] 4,421,862

[45] Dec. 20, 1983

[54] CO HYDROGENATION AND ALCOHOL HOMOLOGATION BY MEANS OF SOLUBLE GROUP VIII HOMOGENEOUS CATALYSTS

[75] Inventor: John S. Bradley, Scotch Plains, N.J.

[73] Assignee: Exxon Research and Engineering Co., Florham Park, N.J.

[21] Appl. No.: 242,639

[22] Filed: Mar. 11, 1981

Related U.S. Application Data

[63] Continuation-in-part of Ser. No. 76,967, Sep. 20, 1979, abandoned, which is a continuation of Ser. No. 917,209, Jun. 20, 1978, abandoned.

[51] Int. Cl.$^3$ .............................................. C07C 27/06
[52] U.S. Cl. .................................................. 518/700
[58] Field of Search ......................................... 518/700

[56] References Cited

U.S. PATENT DOCUMENTS 2,535,060 12/1950 Gresham ............................. 518/700
2,549,470 4/1951 Howk et al. ........................ 518/700
3,833,634 9/1974 Pruett et al. ........................ 518/701
3,957,857 5/1976 Pruett et al. ........................ 518/701

FOREIGN PATENT DOCUMENTS 2644185 4/1977 Fed. Rep. of Germany ...... 518/700

OTHER PUBLICATIONS

Doyle et al., J. Organomet. Chem., 175 C55–C58, 1979.

Primary Examiner—Howard T. Mars
Attorney, Agent, or Firm—James H. Takemoto

[57] ABSTRACT

Hydrogen and carbon monoxide are converted into methanol by means of the catalytic action of soluble ruthenium-carbonyl containing complexes at a temperature of from about 250°–300° C., pressures of from about 54 to 200 MPa and CO/H$_2$ ratio of from 3:1 to 1:10. The soluble ruthenium-carbonyl containing complex is prepared in situ in the reaction medium from sources of ruthenium capable of forming Ru-CO containing complexes.

2 Claims, 5 Drawing Figures

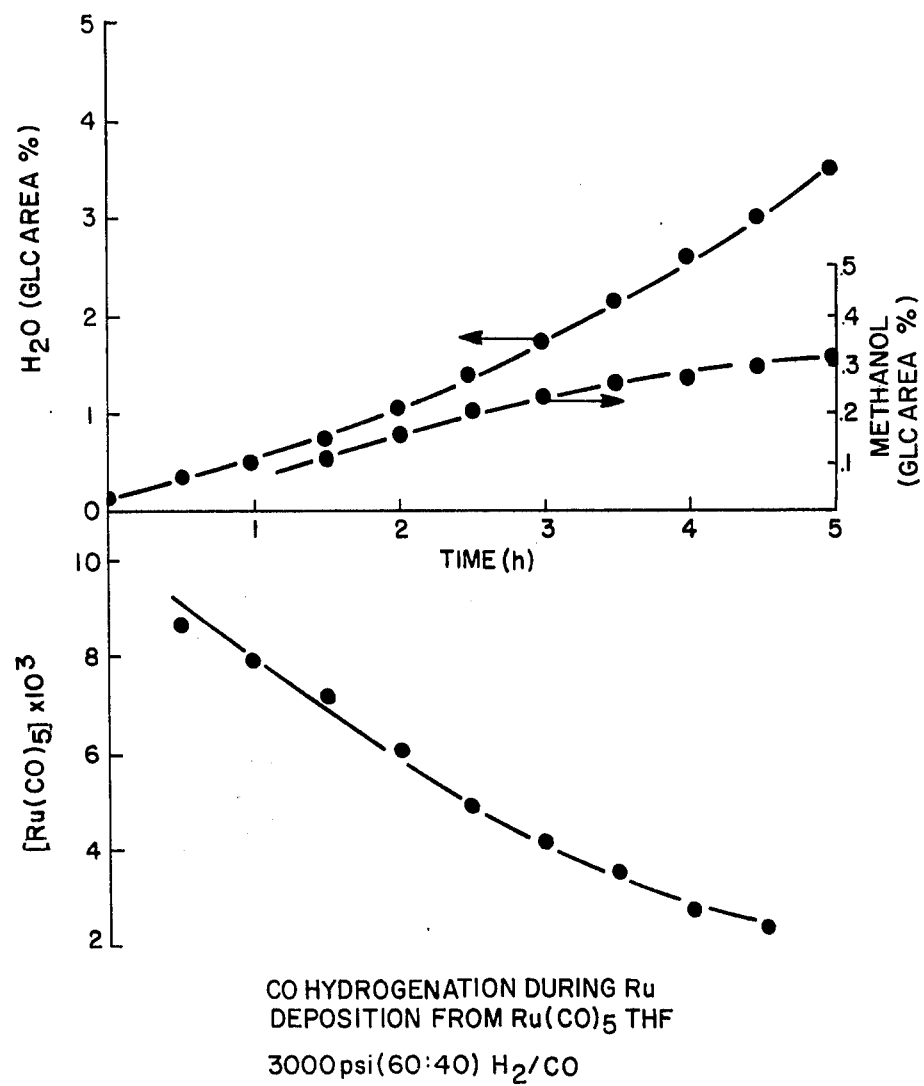
CO HYDROGENATION DURING Ru
DEPOSITION FROM Ru(CO)$_5$ THF
3000 psi (60:40) H$_2$/CO
FIGURE II

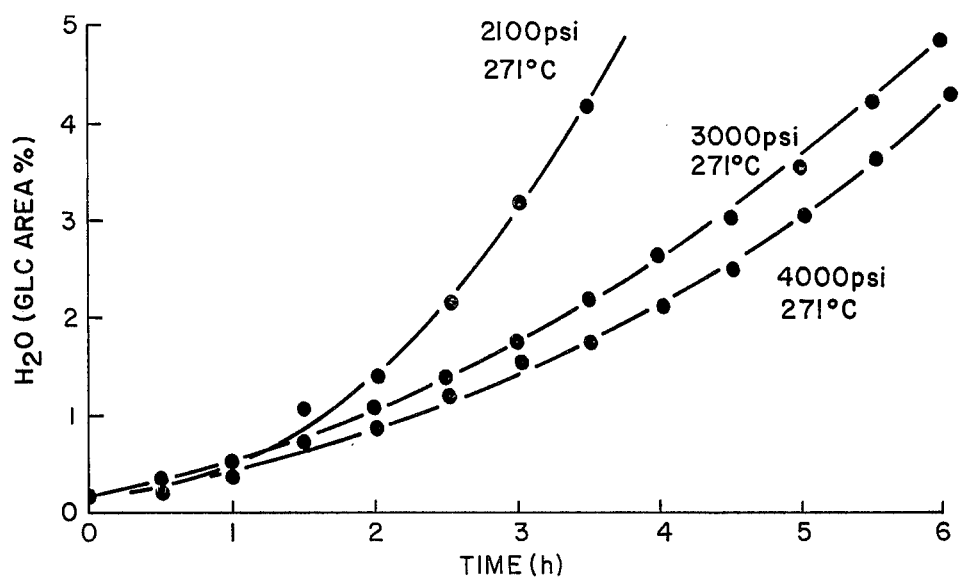
WATER FORMATION DURING Ru DEPOSITION FROM $Ru(CO)_5$
IN THF UNDER $CO/H_2$ (40:60)
FIGURE III

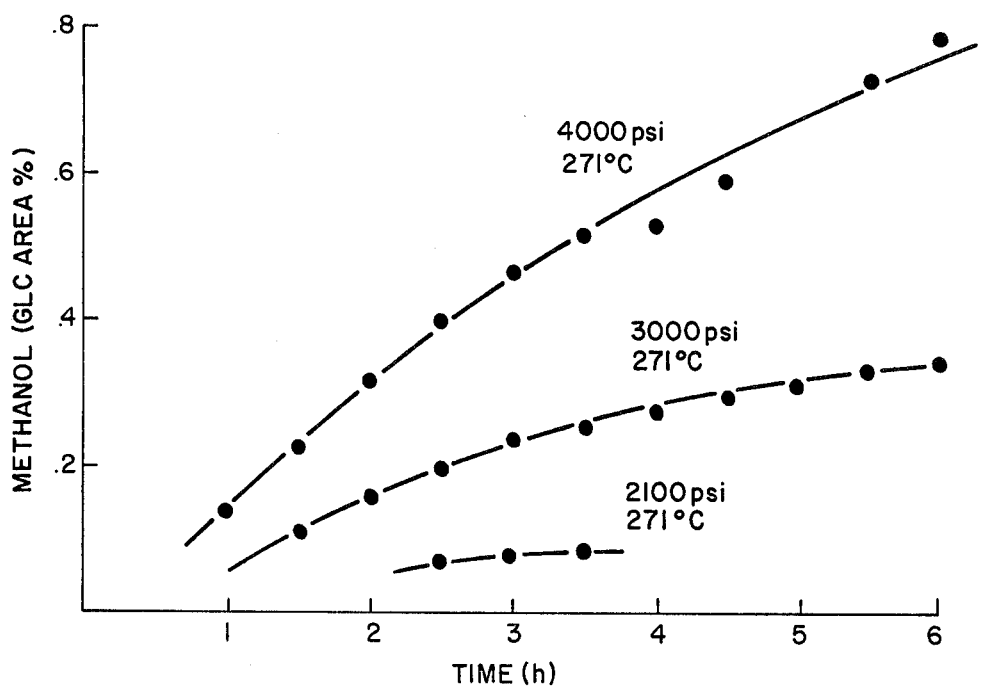
METHANOL FORMATION DURING Ru DEPOSITION FROM Ru(CO)$_5$
IN THF UNDER CO/H$_2$ (40:60)
FIGURE IV

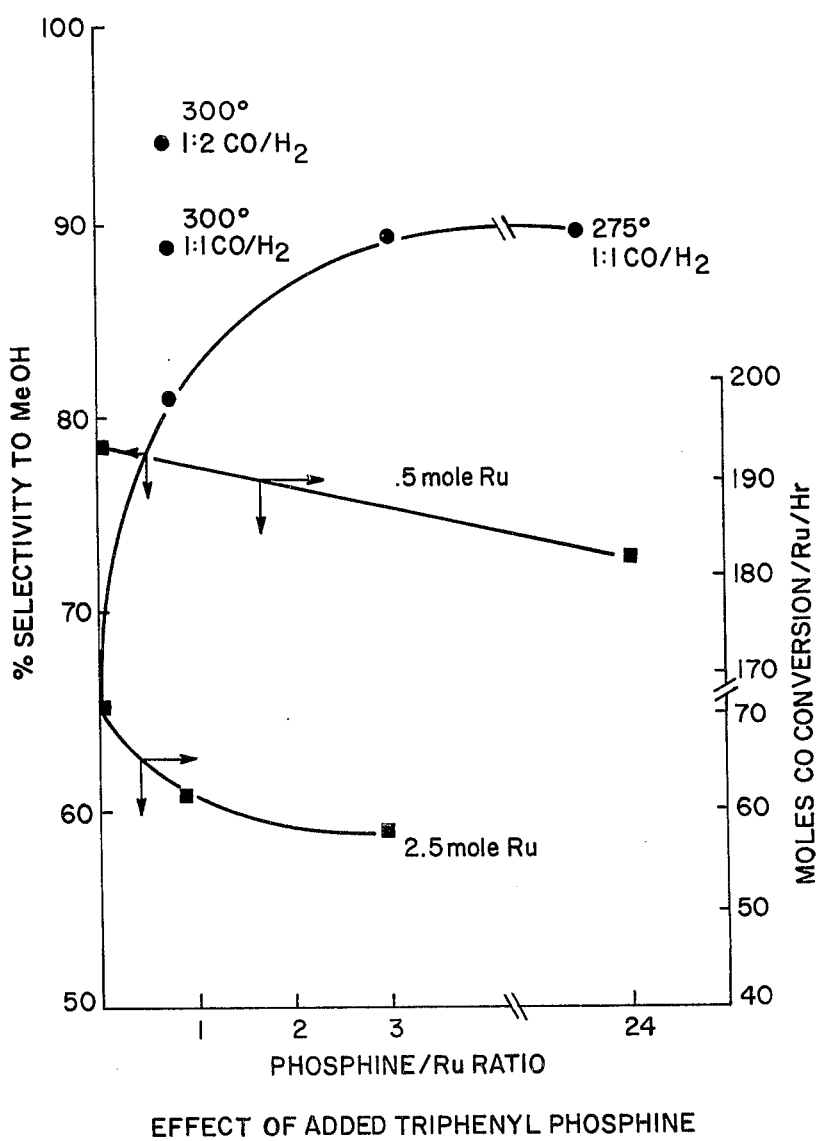
FIGURE V
EFFECT OF ADDED TRIPHENYL PHOSPHINE

CO HYDROGENATION AND ALCOHOL HOMOLOGATION BY MEANS OF SOLUBLE GROUP VIII HOMOGENEOUS CATALYSTS

CROSS-REFERENCE TO RELATED APPLICATIONS

This application is a continuation-in-part of application Ser. No. 76,967 filed Sept. 20, 1979, abandoned, which is a continuation of application Ser. No. 917,209 filed June 20, 1978, abandoned.

It has been discovered, and forms the basis of this disclosure that hydrogen and carbon monoxide can be preferentially converted into methanol by means of the catalytic action of soluble homogeneous ruthenium-carbonyl containing complexes at temperatures of from about 250°–300° C., preferably 250°–275° C., pressures of from about 54 to 200 MPa, preferably 54–140 MPa and $CO/H_2$ ratios of from 3:1 to 1:10, preferably 2:1 to 1:5, most preferably 1:1 to 1:2. The soluble homogeneous ruthenium-carbonyl containing complex is prepared in situ in the presence of the reactants and solvent from many sources of ruthenium. Such ruthenium sources are selected from the group consisting of ruthenium metal or inorganic ruthenium salts preferably the trihalides, oxides, nitrates, sulfates and carbonates; organic ruthenium salts, preferably the formates, acetates, oleates and other carboxylic acid salts; organic ruthenium compounds, preferably ruthenium acetylacetonates, ruthenocene and cyclopentadienyl ruthenium derivatives; carbonyl containing compounds, preferably ruthenium pentacarbonyl, $Ru_3(CO)_{12}$, $Ru_4(CO)_{12}H_4$, $Ru_6(CO)_{18}{}^{2-}$, $Ru_6C(CO)_{17}$ and their derivatives, and other ruthenium compounds capable of forming carbon monoxide containing compounds under reaction conditions (i.e. in the presence of CO under the conditions of temperature and pressure recited above). The more preferred sources are tris(acetylacetonate) ruthenium, $Ru(CO)_5$, $Ru_3(CO)_{12}$, $Ru_4(CO)_{12}H_4$, $Ru_4H_3(CO)_{12}{}^-$, $Ru_4(CO)_{13}H_2$, $Ru_6(CO)_{18}H_2$, $Ru_6(CO)_{18}{}^{-2}$. The most preferred sources are tris(acetylacetonate) ruthenium, $Ru_3(CO)_{12}$, $Ru(CO)_5$.

The ruthenium catalyst is utilized in a solvent, typical solvents being saturated and aromatic hydrocarbons, e.g. $C_6$–$C_{12}$ alkanes, naphtha, decalin, tetrahydronaphthalene, kerosene, mineral oil, cyclohexane, cycloheptane, alkylcycloalkane, benzene, toluene, xylene, naphthalene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of alkylene glycols and polyalkylene glycols, such as ethylene glycol, of propylene glycol, of butylene glycol, of diethylene glycol, of dipropylene glycol, of triethylene glycol, of tetraethylene glycol, of pentaethylene glycol, of dibutylene glycol, of oxyethyleneoxypropylene glycol, etc., preferably, those in which the alkylene group contains 2 carbon atoms in the divalent moiety, such as ethylene and 1,2-propylene; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethyl-hexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; lactones such as γ-butyrolactone and γ-valerolactone, etc.; and others; γ-butyrolactone and the mono and dialkylethers of triethylene and tetraethylene glycol, alcohols, such as $C_1$–$C_{10}$ straight and branch chain alcohols. The only requirement surrounding the choice of a solvent is that at the temperatures and pressures of reaction the solvents are liquids. Preferred solvents are ethers, in particular tetrahydrofuran (THF).

The process of the instant invention results in the preferential formation of methanol as the only alcohol product from CO and hydrogen. In addition, a minor quantity of methyl formate is also generated. The amount of methyl formate produced can be controlled either by the addition of a ligand, such as a phosphine ligand i.e. triarylphosphines (such as triphenylphosphine), trialkyl phosphines, (such as tributylphosphine), tricycloalkylphosphines (such as tricyclohexylphosphine), and mixed alkylarylphosphines such as phenyldimethylphosphine, by operating in the higher temperature range disclosed (i.e. 250°–300° C. or more) or by the downward adjustment of the $CO/H_2$ ratio (i.e. 1:2 $CO/H_2$ or less) or by combinations of the above.

Higher alcohols ($C_2$–$C_5$, preferably $C_2$), acetates or acetaldehydes or acetic acid can be produced by the process recited above, either from the methanol produced and additional CO and hydrogen, or solely from CO and hydrogen, simply by utilizing, in addition to the recited ruthenium-carbonyl complex catalyst, an iodine containing promoter. Suitable iodine promoters include $I_2$, $C_1$–$C_4$ iodide, LiI, NaI, KI, HI, any organic iodide, acyl iodide, ammonium iodide, phosphorous iodide, $RuI_3$, preferably $CH_3I$, $C_2H_5I$, $CH_2I_2$, $C_2H_4I_2$, $RuI_3$.

From this it can be seen that higher molecular weight alcohols ($C_2+$) can be synthesized from CO and $H_2$ simply by permitting the methanol synthesis reaction to proceed in the presence of excess CO and $H_2$ (but within the recited ratios) utilizing the recited homogeneous ruthenium-carbonyl cluster complex catalyst plus a suitable iodine promoter, such as those recited above or by using $RuI_3$ as the ruthenium catalyst precursor in the first place. Temperatures, pressures, solvents and $CO/H_2$ ratios for the production of higher alcohols are those presented for the synthesis of methanol from CO and $H_2$.

In the practice of either methanol synthesis or alcohol homologation the amount of ruthenium catalyst used is not critical and can range between wide extremes. The minimum amount is as little as 0.0001 wt. % ruthenium metal based on the total weight of reaction mixture. The upper limit is on the order of 30 wt. % ruthenium metal based on total weight of reaction mixture, the upper limit being set more by economic factors than any other consideration. Preferably, concentration ranges from 0.1 to 20 wt. %, more preferably 0.5 to 10 wt. % ruthenium metal based on the total weight of the reaction mixture.

In the process, the ruthenium-carbonyl precursor of choice is dissolved in the solvent and subjected to the $CO/H_2$ atmosphere which generates the homogeneous ruthenium-carbonyl complex which is effective in the instant invention. Additional $CO/H_2$ in the proper ratio is introduced over the thus prepared homogeneous catalyst within the recited temperature and in sufficient quantity so as to maintain the desired pressure yielding methanol.

In practicing the generation of higher alcohols, acetates, acetaldehydes or acetic acid the amount of iodine promoter necessary to be effective, based on the amount of ruthenium-carbonyl complex catalyst utilized is in the weight ratio of 10:1 to 1:10, preferably 1:1 to 4:1 iodine to ruthenium, most preferably 2:1 to 0.1 to 1 iodine to ruthenium.

The materials produced by the process of the instant invention include methanol, high alcohols, for example $C_4$-$C_4$, when specifically desired, acetaldehyde, acetates, ether, methyl formate, and gaseous products such as methane, carbon dioxide and unreacted CO and $H_2$. The methanol and higher alcohol products can be separated from the minor amount of coproduced materials be conventinal separation, isolation and purification techniques.

EXPERIMENTAL $Ru_3(CO)_{12}$, $Ru(acac)_3$, $Ru_4H_4(CO)_{12}$ and $(\phi_4As)[Ru_4H_3(CO)_{12}]$ were synthesized by literature methods. $(Et_4N)_2[Ru_6(CO)_{18}]$ was prepared in high yield by the reaction of $Mn(CO)_5^-$ on $Ru_3(CO)_{12}$ in refluxing diglyme.

Solvents were distilled from sodium benzophenone ketyl under nitrogen immediately before use. All manipulations of air-sensitive compounds were performed under nitrogen using standard double-manifold vacuum/nitrogen line techniques.

High pressure experiments up to 33 MPa (5000 psi) were conducted in a 1 liter Autoclave Engineers stainless steel stirred autoclave equipped with liquid sampling line. In a typical run, the catalyst solution was pressured into the autoclave via a blowcase, under syngas (60:40 or 50:50 $H_2$/CO as required), and brought to the desired temperature and pressure. Liquid samples were taken periodically into serum capped glass vials, which had been precooled and wrapped in aluminum foil, and then stored at $-78°$ C. until infrared and glc analysis could be performed. Experiments at pressures up to 120 MPa (18000 psi) were conducted in a 400 cc Autoclave Engineers Hastelloy C stirred autoclave. Liquid sampling was not feasible during the run, and so analyses were performed only at the termination of each experiment.

Infrared spectra were recorded on a Beckmann 4250 spectrophotometer equipped with absorbance accessory, using sealed KBr solution cells fitted with Teflon stopcocks to facilitate analysis of air-sensitive solutions. Gas-liquid chromatography was performed on chromosorb 101 columns, using a Perkin-Elmer 910 chromotograph, equipped with both flame ionization and thermal conductivity detectors.

I. Behavior of Ruthenium Clusters Under CO/$H_2$ $Ru_3(CO)_{12}$, when heated under moderate pressures of CO, is known to break down to monomeric $Ru(CO)_5$. On the other hand, it is known that $Ru_3(C0)_{12}$ when heated under hydrogen pressure, is transformed to a hydride cluster of higher aggregation—$Ru_4H_4(CO)_{12}$. It was therefore necessary to determine the fate of ruthenium clusters under CO/$H_2$ pressure in order to come to any conclusion about the probable species present in any ruthenium catalyzed CO hydrogenation.

When $Ru_3(CO)_{12}$ in tetrahydrofuran solution is subjected to a pressure of 4000 psi CO/$H_2$ (40:60) and heated to 175° C., the cluster is rapidly broken down to mononuclear $Ru(CO)_5$. The infrared bands ($\nu_{co}$) of the cluster at 2065 cm$^{-1}$, 2036 cm$^{-1}$ and 2012 cm$^{-1}$ are completely replaced by absorptions due to $Ru(CO)_5$, at 2000 cm$^{-1}$ and 2035 cm$^{-1}$.

The absorption at 2000 cm$^{-1}$ due to the pentacarbonyl remained of constant intensity within $\pm 2\%$ over a six hour period confirming both the reproducibility of the sampling and analysis method, and the stability of $Ru(CO)_5$ in THF under these conditions (FIG. 1A).

We have observed similarly facile cluster fission for several other ruthenium cluster carbonyls.

II. CO Hydrogenation Catalysts

At temperatures below 200° C., no conversion of CO to hydrogenated products was observed with ruthenium carbonyl solutions and in an attempt to induce such a reaction. Solutions of $Ru(CO)_5$ ca. 10 mM in THF were heated to 271° C. under 3000 psi CO/$H_2$ (40:60). Under these conditions, the concentration of $Ru(CO)_5$, measured again by the absorbance of the solution at 2000 cm$^{-1}$, fell to 2.5 mM over six hours (FIG. 1C), indicating metal deposition; that metal deposition had occurred was confirmed on examining the autoclave at the end of the run. Analysis of liquid samples revealed the presence of water, methanol and saturated hydrocarbons up to $C_{30}$, and a gas sample taken at the end of the run contained, in addition to CO and $H_2$, methane plus small amounts of $CO_2$ (produced via a water gas shift). There are thus two predominant CO hydrogenation processes occurring:

i. $CO+2H_2 \rightarrow CH_3OH$
ii. $nCO+(2n+1)H_2 \rightarrow C_nH_{2n+2}+H_2O$ Since neither dimethyl ether nor methanol homologation products were detected in the product mixture, hydrocarbon synthesis is the predominant source of water in the system, and so water concentration could be used as a convenient indirect measure of total hydrocarbon concentration.

The nature of the catalysts involved in each reaction are identifiable by correlating the rates of methanol and water formation with the concentration of ruthenium in solution, measured as $Ru(CO)_5$. A plot of the time dependence of the concentrations of $Ru(CO)_5$, methanol and water is shown in FIG. 2. The rate of methanol formation decreases with the falling concentration of $Ru(CO)_5$, implying that the methanol synthesis homogeneously is catalyzed by a soluble ruthenium complex. In contrast with the homogeneous reaction, the rate of formation of hydrocarbon (measured as indirectly as water) increases as the concentration of $Ru(CO)_5$ falls and ruthenium metal deposition proceeds; the hydrocarbon synthesis observed in this system is thus identified as a heterogeneously catalyzed reaction, occurring on the surface of metallic ruthenium.

It is known that ruthenium metal reacts with CO above 200° C. at ~3000 psi to yield $Ru(CO)_5$ in low yields and so the equilibrium:

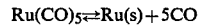

$Ru(CO)_5 \rightleftharpoons Ru(s)+5CO$ may be envisaged, although no quantitative equilibrium constant data are available. The extent of metal deposition in the system should therefore be determined by the partial pressure of CO; the validity of the conclusions reached above on the basis of the experiments at 3000 psi was therefore tested by repeating the run at 2100 psi and 4000 psi, (60:40, $H_2$:CO) at 270° C. As expected, the rate of ruthenium deposition was greatest at the lower pressure dropping from 10 mM to ~1 mM in 3.5 hours (FIG. 1d) and the rate of hydrocarbon formation increased at a correspondingly greater rate than that observed at 3000 psi (FIG. 3); the rate of methanol formation was suppressed and decreased more markedly as the run progressed (FIG. 4). At 4000 psi the greater CO partial pressure maintained the ruthenium as soluble pentacarbonyl more effectively than at the lower pressures, and over a six hour run, the concentration of Ru(CO)$_5$ fell from 10 mM only to 7.5 mM (FIG. 1b). Metal deposition had occurred only to 30% of that observed at 3000 psi and again as expected the rate of hydrocarbon formation was suppressed, (FIG. 3) while methanol was formed at a higher rate than at 3000 psi and tailed off less markedly with time (FIG. 4). These results obtained at 2100 psi and 4000 psi confirm the conclusions reached on the basis of the 3000 psi run that hydrocarbon formation is heterogeneously catalyzed by ruthenium metal in this system, whereas methanol formation is homogeneously catalyzed by a soluble ruthenium species.

Under the temperature and pressure conditions set forth for FIGS. 1 and 3 above, some metal deposition was observed at longer reaction times due to insufficient CO partial pressure. In order to stabilize the ruthenium complex against decomposition to metal, it is necessary to raise the pressure to about 8000 psi (50:50 H$_2$:CO) at 275° C. As shown in Example 1b, no hydrocarbon was observed after four hours heating due to heterogeneous catalysis by metal. Therefore the pressure range for the homogeneously catalyzed synthesis of methanol and methyl formate is from about 54 MPa (8000 psi) to 200 MPa.

Although the soluble ruthenium was observed and measured as Ru(CO)$_5$, it could not be deduced, on the basis of the evidence obtained that the catalytically active species contained only one ruthenium atom. Despite the fact that no polynuclear clusters were detected in liquid samples taken during the run, the actual analyses were performed under ambient conditions, and the presence of clusters in low concentrations under reaction conditions could not be excluded.

(i) Catalyst Precursor:

As at the lower pressures, a number of neutral and anionic ruthenium complexes were screened at 120 MPa, (18,000 psi) including Ru$_3$(CO)$_{12}$, Ru$_4$H$_4$(CO)$_{12}$, [Ru$_4$H$_3$(CO)$_{12}$]$^-$, [Ru$_6$(CO)$_{18}$]$^{2-}$ and Ru(acac)$_3$, and all were carbonylated predominantly to Ru(CO)$_5$ under the conditions employed. Since no apparent purpose was served by using clusters as catalyst precursors, a readily available Ru(CO)$_5$ precursor was used for subsequent runs; ruthenium tris (acetylacetonate) is an air stable complex of ruthenium prepared in high yield from ruthenium trichloride, and it is readily transformed to ruthenium carbonyl complexes by CO/H$_2$ mixtures at temperatures and pressures well below our reaction conditions.

Under the chosen base case conditions of 18,000 psi CO/H$_2$ (1:1), 275° C., 1.67×10$^{-2}$ M Ru (added as Ru(acac)$_3$) is tetrahydrofuran, no hydrocarbon formation is observed, methanol synthesis is rapid and methyl formate is the only byproduct formed in significant amounts. These two CO hydrogenation products comprise >99% of the liquids formed in the process, with a turnover rate (CO→CH$_3$[31]) of ~70/hr. per Ru atom and 66% selectivity to methanol.

(ii) Temperature

Under 18,000 psi CO/H$_2$ (1:1) little activity is observed below 250° C., at which temperature 14.4 moles/hr. CO are converted per mole ruthenium, with a selectivity of 62% to methanol. Methyl formate is the only other product formed. At 275° C. activity and selectivity increase, the turnover number rising to 70 with a selectivity to methanol of 66%. At 300°, some methanation was observed, implying metal deposition, but activity and selectivity (among liquid products) again improved, (77 turnovers/hr. 86% to methanol).

(iii) Feed Gas Composition

Both selectivity and activity are sensitive to the composition of the feed gas. An increase in CO partial pressure from 60 MPa (base case) to 90 MPa (i.e. CO/H$_2$ increase from 1 to 3) suppresses activity completely. An increase in CO partial pressure effectively adds a high concentration of blocking ligand to the system, and the hydrogenation reaction is thereby inhibited. A CO/H$_2$ ratio of 0.5 (40 MPa CO) results in a slight activity increase (73 turnovers/Ru/hr.) and a significant selectivity increase (80% of MeOH, cf 66% using 1:1 CO/H$_2$).

(iv) Phosphine Promotion

The selectivity to methanol is also markedly affected by the addition of triphenylphosphine to the reaction mixture. As would be expected from the suppression of activity under high CO partial pressures, activity is lower in the presence of added triphenylphosphine, a good ligand for low valent transition metal complexes. However, the phosphine ligand exerts a further control over the course of the reaction and appears to inhibit the formation of methyl formate to some degree, thus enhancing the selectivity to methanol, which reaches a maximum of 88% at a phosphine to ruthenium ratio of 3 (FIG. 5) under base case conditions, with a slght decrease in activity (turnover/h CO→CH$_3$=54), compared with a selectivity of 66% (71) in the absence of phosphine.

By combining the beneficial effects of phosphine promotion with those of a hydrogen rich feed and higher temperature, selectivity to methanol can be raised to 94% at 300°, 2:1 H$_2$/CO at a phosphine to ruthenium ratio of 3:1 (FIG. 5).

(v) Iodine Promotion

By adding iodine in the form of I$_2$, lithium iodide or methyl iodide to the system, the reaction shifts from exclusively C$_1$ products to mainly C$_2$, and a direct synthesis of ethanol from syngas is observed under the standard operating conditions.

EXAMPLES OF METHANOL SYNTHESIS

EXAMPLE 1

(a) a 400 cc stirred autoclave was charged with a solution of Ru(acac)$_3$ (1.0 g) in THF (150 ml). After purging with 1:1 CO/H$_2$ the system is sealed and brought to 250° and 120 MPa total pressure. Additional gas was added as necessary over a 4.5 hour reaction time to maintain a pressure of 120 MPa, while the temperature was maintained at 250° C. The system was allowed to cool to room temperature, and after venting to 2 MPa, gas and liquid samples were taken and analyzed by gas chromatography. The liquid product contained 4 g methanol and 2.2 g methyl formate. The gas phase contained only carbon monoxide and hydrogen.

(b) The autoclave was charged with a solution of one gram of Ru(acac)$_3$ in 250 ml THF. Using the procedure of part (a), the reactor was charged with 1:1 CO/H$_2$ at a pressure of 8000 psi (54 MPa) and a temperature of 275° C. After four hours, the reaction was analyzed and found to contain 6.9 g methanol and 1.8 g methyl formate. No water or hydrocarbon was detected, indicating that 54 MPa total pressure (27 MPa CO partial pressure) is sufficient to stabilize the soluble ruthenium complex against decomposition to metal.

EXAMPLE 2

As in Example 1, the reaction temperature being 275° C. The liquid product contained 17.2 g methanol, 16.2 g methyl formate. The gas phase contained detectable amounts of methane and carbon dioxide in addition to carbon monoxide and hydrogen.

EXAMPLE 3

As in Example 1, the reaction temperature being 300° C. The liquid product contained 26.0 g methanol, 3.7 g methyl formate, 9 g water and small amounts of ethanol. The gas phase contained substantial amounts of methane and carbon dioxide in addition to carbon monoxide and hydrogen.

EXAMPLE 4

As in Example 2, the feed gas being 1:2 $CO/H_2$. The liquid product contained 21 g methanol, 10 g methyl formate.

EXAMPLE 5

As in Example 2, with the addition of 2.0 g triphenyl phosphine. The liquid product contained 18.6 g methanol, 4.7 g methyl formate. The gas phase contained only carbon monoxide and hydrogen.

EXAMPLE 6

As in Example 1, with the addition of 0.5 g triphenyl phosphine, the temperature being 300° C. Liquid product contained 37 g methanol, 10.3 g methyl formate. The gas phase contained detectable amounts (<1%) of methane and carbon dioxide in addition to carbon monoxide and hydrogen.

EXAMPLE 7

As in Example 6, the feed gas being 1:2 $CO/H_2$. Liquid product contained 29 g methanol, 3.3 g methyl formate, 5 g water, and small quantities of ethanol. The gas phase contained methane and carbon dioxide in addition to carbon monoxide and hydrogen.

EXAMPLES OF METHANOL HOMOLOGATION

EXAMPLE 8

A solution of $Ru(acac)_3$ (1.0 g) and iodine (0.25 g) in tetrahydrofuran (130 g) was charged into a 400 cc stirred autoclave. After purging with syngas (1:1 $CO/H_2$) the system was brought to 275° C. and 120 MPa total pressure. Gas was added as necessary to maintain the pressure at 120 MPa. After 4.5 hours, the system was allowed to cool to room temperature, and after venting to 2 MPa, gas and liquid samples were taken and analyzed by gas chromatography. The liquid product contained, in addition to THF, water (40 g), methanol (15 g), ethanol (20 g) and propanol (2 g) plus substantial amounts of THF derived products—n-butanol, n-pentanol and n-hexanol. The gas phase contained, in addition to carbon monoxide and hydrogen, substantial quantities of carbon dioxide and methane.

EXAMPLE 9

As in Example 1, but using methanol (120 g) as solvent, and lithium iodide (0.37 g) as promoter. The liquid product contained methanol (73 g), ethanol (58 g), n-propanol (3.5 g) and water (37 g) in addition to small amounts (<1%) of ethers, formates and acetates of the alcohols present. The gas phase contained methane, ethane, carbon dioxide, in addition to carbon monoxide and hydrogen.

EXAMPLE 10

This example explored the use of toluene as the solvent. 1.0 g $Ru(acac)_3$, 0.25 g iodine, in 150 ml toluene were reacted at 120 MPa with 1:1 $CO/H_2$ at 275° C. for five hours. The liquid product was a two-phase system. The organic phase contained 1.9% $H_2O$, 11.5% methanol, 1.8% ethanol, 83% toluene. The aqueous phase contained 17% $H_2O$, 51% methanol, 7.5% ethanol and 21% toluene.

What is claimed is:

1. A process for the homogeneous catalytic synthesis of methanol and methyl formate from CO and hydrogen consisting essentially of contacting CO and $H_2$ with a catalytic system comprising essentially of a soluble ruthenium carbonyl containing complex plus a phosphine in a solvent selected from the group consisting of saturated and aromatic hydrocarbons, ethers, carboxylic acids, alkanols, ketones, esters and lactones at a temperature of from about 250° to 300° C., a pressure of from about 54 to 200 MPa and a CO to $H_2$ ratio of from 3:1 to 1:10.

2. A process for the homogeneous catalytic synthesis of methanol and methyl formate from CO and $H_2$ consisting essentially of contacting CO and $H_2$ with a catalytic system consisting essentially of Ru(acetylacetonate)$_3$, $Ru_3CO_{12}$ and $Ru(CO)_5$ plus a phosphine in a solvent selected from the group consisting of saturated and aromatic hydrocarbons, ethers, carboxylic acids, alkanols, ketones, esters and lactones at temperatures of from about 250° to 300° C., a pressure of from about 54 to 200 MPa and a CO to $H_2$ ratio of from 3:1 to 1:10.

* * * * *